United States Patent [19]
White et al.

[11] Patent Number: 5,461,417
[45] Date of Patent: Oct. 24, 1995

[54] CONTINUOUS DIFFUSE ILLUMINATION METHOD AND APPARATUS

[75] Inventors: Timothy P. White, New Boston; Michael C. Messina, Goffstown; Steven M. LeBlanc, Hancock, all of N.H.

[73] Assignee: Northeast Robotics, Inc., New Boston, N.H.

[21] Appl. No.: 131,695

[22] Filed: Oct. 5, 1993

Related U.S. Application Data

[63] Continuation-in-part of Ser. No. 18,233, Feb. 16, 1993, abandoned.
[51] Int. Cl.$^6$ .................................................. H04N 7/18
[52] U.S. Cl. .......................... 348/131; 348/125; 348/126; 348/87; 348/92; 382/141
[58] Field of Search .................................... 348/86, 87, 92, 348/131, 126, 91, 125, 128, 133, 88; 382/141; H04N 7/18

[56] References Cited

U.S. PATENT DOCUMENTS

| | | | |
|---|---|---|---|
| 3,322,487 | 9/1966 | Renner | 89/352 |
| 3,558,894 | 1/1971 | Odone et al. | 261/350 |
| 4,067,026 | 1/1978 | Pappanikolaou | 77/354 |
| 4,139,306 | 2/1979 | Norton | 348/131 |
| 4,341,449 | 7/1982 | Iwata et al. | 126/354 |
| 4,677,473 | 6/1987 | Okamoto et al. | 348/131 |
| 5,064,291 | 11/1991 | Reiser | 348/131 |
| 5,172,005 | 12/1992 | Cochran et al. | 348/88 |
| 5,187,611 | 2/1993 | White | 348/131 |

*Primary Examiner*—Tommy P. Chin
*Assistant Examiner*—Vu Le
*Attorney, Agent, or Firm*—Davis, Bujold & Streck

[57] ABSTRACT

The invention pertains to a method and apparatus for providing a continuous, uniform, diffuse lighting environment for use in conjunction with electronic machine vision, or manual microscope inspection systems to inspect specular surfaces such as soldered circuits, ball bearings, reflective packaging, relective packaging, etc. The disclosed invention effectively eliminates apparent variations in surface brightness caused by the reflection of discontinuities in traditional machine vision lighting systems that typically require windows or viewing openings or orifices to allow visual access to the object being observed, thus allowing for a true observation signal from which the effect of surface geometry has been substantially removed. The object being observed is illuminated using a diffuse lighting system that comprises, in combination, an on-observation axis diffuse light source and an off-observation axis light source each controlled under separate brightness control such that a substantially uniform diffuse lighting environment is created over the entire object.

32 Claims, 8 Drawing Sheets

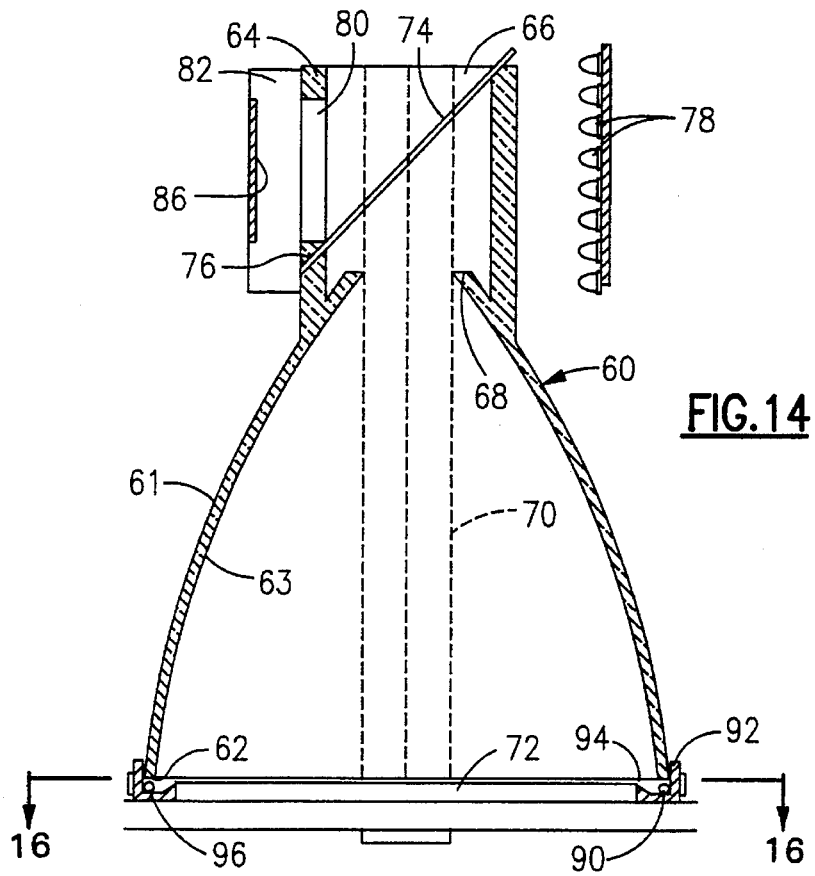
FIG. 14
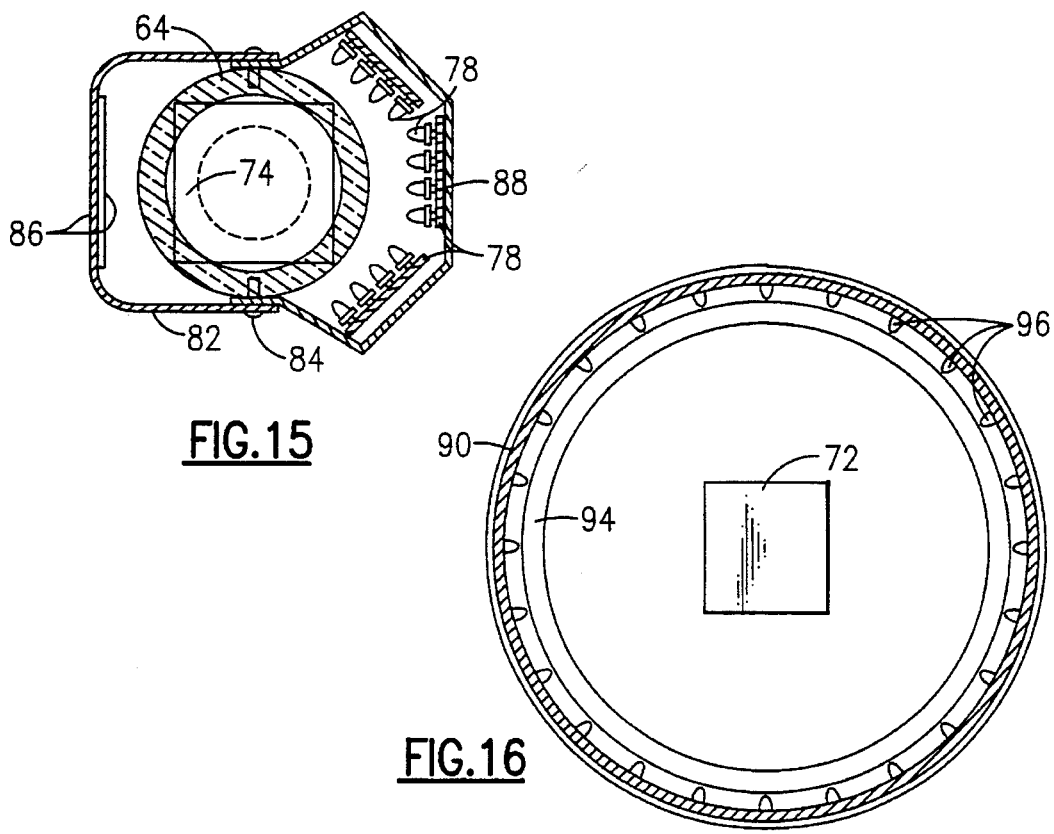
FIG. 15
FIG. 16

CONTINUOUS DIFFUSE ILLUMINATION METHOD AND APPARATUS

RELATED APPLICATION

This is a continuation-in-part application based upon my application Ser. No. 08/018,233, filed Feb. 16, 1993, entitled Continuous Diffuse Lighting Fixture now abandoned.

BACKGROUND OF THE INVENTION

1. Field of the Invention

The invention pertains to a method and apparatus for permitting electronic machine vision of light reflecting objects wherein a true observation of the surface being viewed is obtained by masking potential reflections resulting along the observation axis due to observation windows and cameras, or other non-illuminating discontinuities in the illumination environment.

2. Description of the Related Art

Electronic machine vision apparatus is commonly employed in conjunction with automatic machining, assembly and inspection apparatus, particularly of the robotic type. Television cameras are commonly employed to observe the object being machined, assembled, or inspected, and the signal received and transmitted by the camera can be compared to a standard signal or database to determine if the observed article is properly machined, oriented, or assembled. Also, machine vision apparatus is widely used in inspection and flaw detection applications whereby inconsistencies and imperfection in both hard and soft goods can be rapidly ascertained and adjustments or rejections instantaneously effected.

Machine vision apparatus detects abnormalities by comparing the signal generated by the camera with a predetermined signal indicating proper dimensions, appearance, orientation, or the like. In order to achieve consistent and accurate results when using machine vision apparatus employing electronic cameras, it is very important that consistent and uniform lighting of the observed object occur, as the lighting will seriously affect the vision signal generated and produce irregular signals even though no fault may exist in the object being observed other than it is not uniformly illuminated.

Illumination problems in machine vision applications are particularly present when the object being observed has a shiny specular surface. For instance, in the inspection of soldered circuits such as used with printed circuit boards the highly reflective nature and uneven surface geometry of the solder makes it very difficult to obtain an accurate electronic signal, and the same is true when machine vision inspecting ball bearings, reflective packaging, and other objects having shiny surfaces, particularly irregular shiny surfaces.

When utilizing machine vision techniques and apparatus in shiny surface applications, it is common to employ complicated lighting systems for illuminating the object being observed, and it is a purpose of such lighting systems to eliminate shadows, highlights, underlights, reflections and other lighting characteristics caused by shiny convex surface objects. Examples of complex lighting systems for use with machine vision apparatus are shown in U.S. Pat. Nos. 4,677,473; 4,882,498; 5,051,825; 5,060,065 and 5,072,127. While devices shown in these patents are capable of generating improved lighting characteristics, such devices do not eliminate erroneous signals resulting from the reflection of windows, openings or orifices defined in the lighting apparatus necessary to permit observation of the article being viewed, and such apparatus does not eliminate erroneous signals generated due to the reflection of cameras, openings or voids from specular objects.

OBJECTS OF THE INVENTION

It is an object of the invention to provide a method and apparatus for illuminating an object to be observed by machine vision cameras wherein a diffused illumination of the object is produced which is continuous in nature and is free of dark or void portions capable of generating erroneous vision signals.

Another object of the invention is to provide a method and apparatus for illuminating specular objects to be observed by electronic machine vision cameras, film cameras, or human observers, wherein the object is uniformly illuminated by a primary, off-observation axis source of diffused light emitting from an envelope substantially surrounding the object, having an observation window or viewing orifice to permit vision access along an observation axis that is masked against reflection by the object.

Another object of the invention is to provide a method and apparatus for illuminating specular objects to be observed by electronic machine vision cameras wherein the object is illuminated by a diffused light emitting from an off-observation axis diffuse light source of a shape and size sufficient to provide substantially uniform illumination of the object to be observed and an on-observation axis diffuse light source projected through an observation window in the off-observation axis diffuse light source to permit machine vision along an observation axis while masking the observation window against possible reflection from the observed object surface.

Yet another object of the invention is to provide a method and apparatus for illuminating machine vision observed specular objects with a uniform diffused light wherein the observation window is masked against possible reflection from the observed object surface by the introduction of a diffused light through the window along the observation axis of an intensity and character substantially equal to the intensity and character of the primary diffused light illuminating the object.

An additional object of the invention is to provide a method and apparatus for masking vision observation windows against possible reflection in the surface of observed articles by projecting a light through the window substantially identical in character to the primary light illuminating the object.

Still another object of the invention is to provide a method and apparatus for illuminating a machine vision illuminated object having a light reflecting surface wherein a beam splitter is employed to project a diffused light through a camera observation window along the camera observation axis of an intensity and character corresponding to the primary diffused light illuminating the observed object.

Yet a further object of the invention is to minimize the depth of the on-observation axis light source assembly by utilizing a curved beamsplitter.

SUMMARY OF THE INVENTION

The practice of the concepts of the invention are primarily utilized in machine vision applications with objects having specular surfaces, including surfaces of convex configurations and surfaces containing numerous convex and concave texture elements such as those found in materials such as embossed metal foil and the like. However, it will be appreciated that the inventive concepts disclosed herein are applicable to film camera and microscope-aided human inspection systems as well.

The object to be machine vision observed, such as the solder of a printed circuit, a ball bearing, or the like, is illuminated from a given side and given direction by a primary off-observation axis light diffusing source. One form that this primary off-observation axis light diffusing source may take is the form of a translucent dome superimposed over the object which is formed of a translucent material and is backlighted by lamps, or the dome may include an inner light diffusing surface or layer, and an outer light reflecting layer whereby light interiorly projected into the dome is diffused and uniformly illuminates the object over which the dome is superimposed. Another form that the primary off-observation axis light diffusing source may take is the form of a ring-shaped diffuse light source. In fact, the primary off-observation axis light diffusing source may take the form of any suitable shape and size to correspond to the shape and size of any given object to be observed so that the entire object to be observed, or any specific region of said object is substantially uniformly illuminated.

In either embodiment, an observation window or windows, which may be in the form of one or more camera openings or orifices, or other zones of material that appears transparent to a machine vision camera, must be defined in the primary diffuse light source whereby the camera, which is located outside the confines of the primary diffuse light source, may have vision access to the object that is located within the primary light source. The line of sight from the camera through the observation window to the object constitutes an observation axis. To prevent the observation window or windows, and the cameras, from reflecting from the surface of the object being observed, and hence creating a false or erroneous signal indicating a fault, a diffused light projector utilizing a flat or curved beam splitter is associated with each observation window to project a secondary, on-observation axis diffused light through the observation window and upon the observed object that is of an intensity and character substantially equal to the diffused light being cast upon the object by the primary diffuse light source, and in this manner the observation window(s), and camera(s) associated therewith, are masked against reflection in the surface of the object being observed by the camera or cameras. Accordingly, by masking the observation window, false signals or reflections from the observed object are prevented and a true camera signal is received capable of accurately interpreting the condition of the observed object free of missignals due to reflections of the lighting or observing apparatus.

Preferably, the diffused light projector is in the form of a beam splitter including a partially silvered mirror or a half silvered membrane pellicle of nitrocellulose or plastic film such as "MYLAR", which has advantageous beam splitting characteristics in certain applications, a light generator, and a light diffusing panel wherein diffused light passing through the diffusing panel is reflected by the partially silvered mirror or membrane through the observation window along the observation axis. As the mirror is light pervious, the camera continues to observe the object through the beam splitter mirror and accurately records the surface conditions of the observed object.

In the practice of the invention, a beam splitter similar to those shown in my co-pending application Ser. No. 07/750, 257 filed Aug. 27, 1991, now U.S. Pat. No. 5,187,611 may be employed. The beam splitter light generator may take several forms as shown in the aforementioned patent, such as incandescent bulbs, diodes, fiber optics, or the like, and in the practice of the invention control means permit accurate control and variation of the diffused light being generated and reflected by the beam splitter in order to equate the beam splitter projected light to that supplied by the primary diffused light source.

As will be appreciated from the following description, the apparatus permitting the practice of the invention is relatively simple and inexpensive as compared with prior art devices incapable of providing a true continuous diffused light as provided by the invention.

BRIEF DESCRIPTION OF THE DRAWINGS

The aforementioned objects and advantages of the invention will be appreciated from the following description and accompanying drawings wherein:

FIG. 14 is a diametrical elevational sectional view of another embodiment of a dome envelope having an inner light diffusing surface wherein a ring is mounted at the lower end of the dome and a plurality of lamps are mounted on the ring, the ring including a reflecting surface for reflecting light upwardly into the envelope upon the inner dome diffuse reflecting surface, FIG. 15 is a plan view of the embodiment of FIG. 4 as taken from the top of FIG. 4, the neck of the dome being shown in section, FIG. 16 is a plan sectional view taken along Section 16—16 of FIG. 14.

DESCRIPTION OF THE PREFERRED EMBODIMENTS

FIGS. 1–6 depict various illumination geometries that have been traditionally used in machine vision systems along with their associated incident angle brightness histograms. For example, in FIG. 1, a co-axial illumination system 1 is employed to illuminate object 2 as it is viewed by electronic machine vision camera 3. As can be seen from the incident angle brightness histogram shown in FIG. 2, this co-axial illumination system provides a diffuse illumination zone 4 with a desirable incident illumination level that coincides with a zero angle of incidence off of the observation axis but is substantially devoid of any illumination as the angle of incidence deviates from zero.

Figure 3:
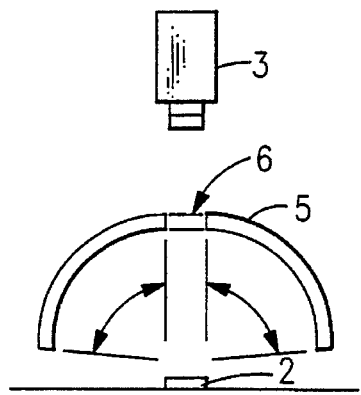
Figure 4:
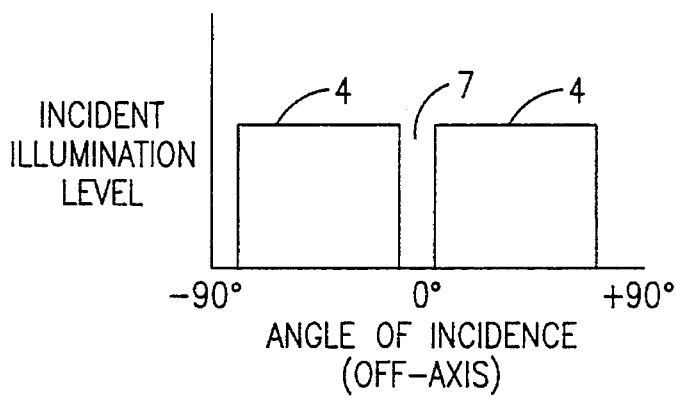

FIG. 3 depicts an off-illumination-axis diffuse dome lighting system 5 illuminating an object 2 to be observed by electronic machine vision camera 3 through an observation window 6, which can be an opening or orifice or even a zone of material that appears transparent to a machine vision camera, such as clear plastic or the like. This illumination system creates the uniform diffuse illumination zone 4 shown in FIG. 4. While the incident illumination level is substantially uniform as the angle of incidence of the light increases away from a zero angle of incidence off of the observation axis, the on-observation axis region 7, which has an angle of incidence approaching zero degrees off-axis, is substantially devoid of any illumination.

Figure 5:
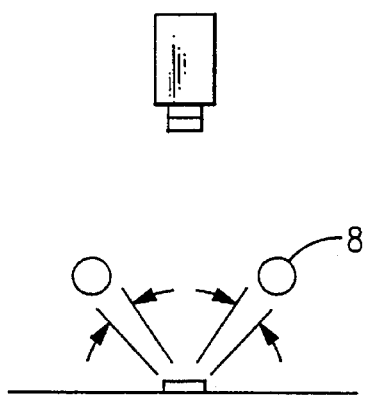
Figure 6:
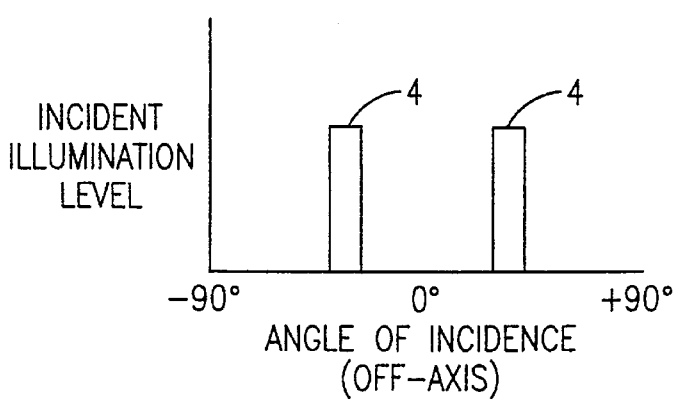
Figure 8A:
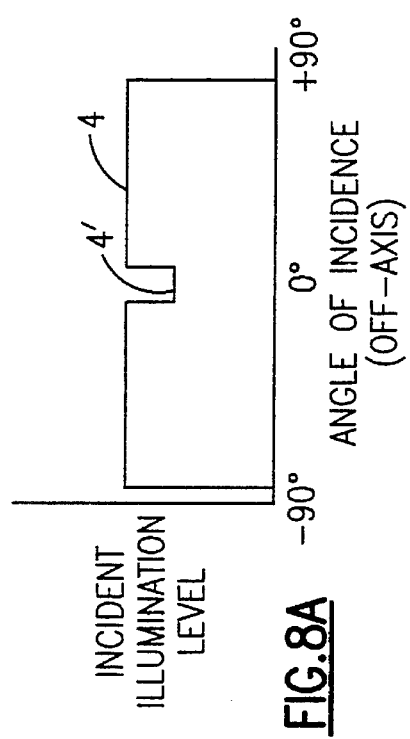
FIGS. 8A and 10A depict the Incident Angle Brightness Histograms associated with the lighting geometries depicted in FIGS. 7A and 9A respectively.
Figure 8:
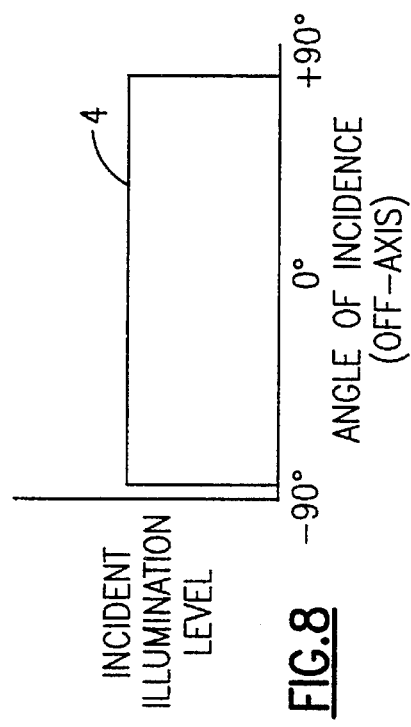
FIGS. 8 and 10 depict the Incident Angle Brightness Histograms associated with the lighting geometries depicted in FIGS. 7 and 9 respectively.

The ring illumination system and its corresponding incident angle brightness histogram, as depicted in FIGS. 5 and 6 respectively, provides a uniform diffuse illumination zone 4 with a substantially uniform incident illumination level that corresponds to substantially the same shape as the ring illuminator 8 being employed.

Figure 7A:
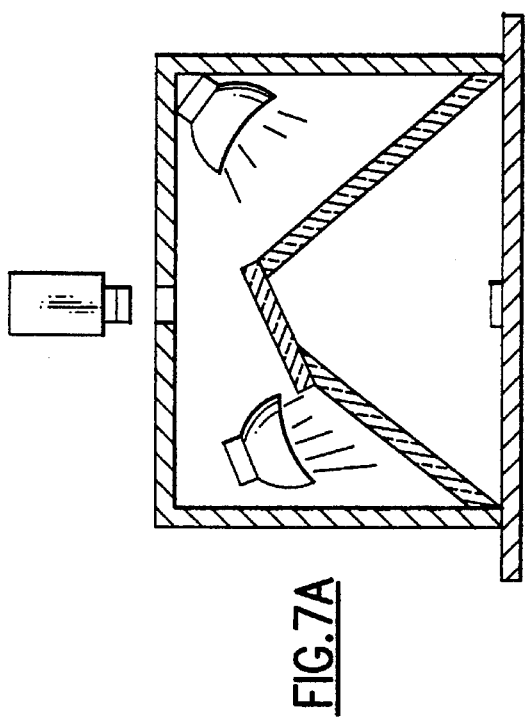
FIGS. 7A and 9A depict two illumination geometries that approach the objectives of the applicants' invention with simple devices that utilize a single light source.
Figure 7:
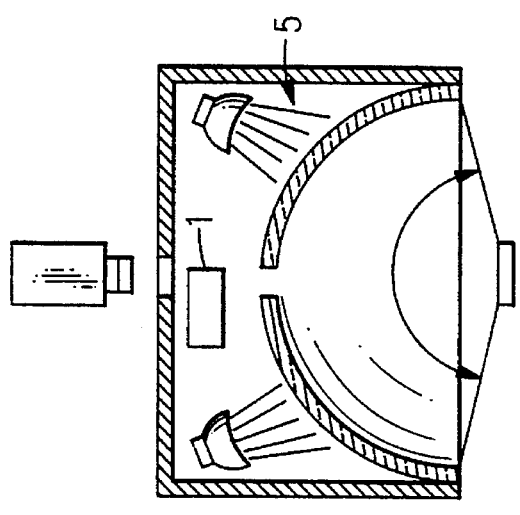
FIGS. 7 and 9 depict two embodiments of Continuous Diffuse Illumination geometries contemplated by the applicants' invention.

FIGS. 7, 7A, 8, 8A, 9, 9A, 10 and 10A show four embodiments of illumination systems and methods contemplated by the present invention and their respective incident angle brightness histograms. First, FIG. 7 shows a dome-shaped continuous diffuse illumination system that is comprised of a combination of the co-axial illumination system 1 of FIG. 1 and the off-illumination-axis diffuse dome lighting system 5 of FIG. 3. The combination of these two illumination systems results in a lighting environment with the incident angle brightness histogram shown in FIG. 8. This environment is characterized by a diffuse illumination zone 4 with a substantially uniform incident illumination level irrespective of the angle of incidence.

FIG. 7A shows a simple, cone-shaped diffuse illumination system that approximates the results obtained using the embodiment of FIG. 7. This embodiments comprises an off-illumination-axis diffuse conical lighting system similar to the dome-shaped lighting system 5 of FIG. 3. This embodiment replaces the secondary diffuse light source with a simple beam splitter that is angularly located in the observation window. This beam splitter arrangement thus operates to reflect a portion of the diffuse light projected through the cone from the off-observation-axis diffuse light source, while at the same time allowing vision access to the object being observed by an observation means that is located outside of the cone-shaped diffuse illumination system. This embodiment results in a lighting environment with the incident angle brightness histogram shown in FIG. 8A. This environment is characterized by a diffuse illumination zone 4 with a brightness level reduced in proportion to the transmissivity of the beam splitter employed. The zone of reduced brightness 4' corresponds to the angles of incidence associated with the beam splitter. For example, a beam splitter with a reflectance-to-transmissivity ratio of 50:50 results in a lighting environment characterized by a histogram showing a 50 percent brightness level associated with those angles corresponding to the angles of incidence associated with the beam splitter. Likewise, if a beam splitter with a 70:30 reflectance-to-transmissivity ration is employed, a lighting environment is created that exhibits a 70 percent brightness level corresponding to the angles of incidence associated with the beam splitter.

Figure 1:
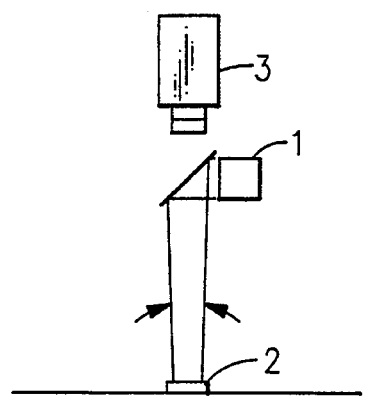
FIGS. 1, 3, and 5 depict traditional illumination geometries used in conjunction with machine vision systems, namely Co-Axial Illumination, Off-Axis Diffuse Dome Illumination, and Ring Illumination respectively.
Figure 2:
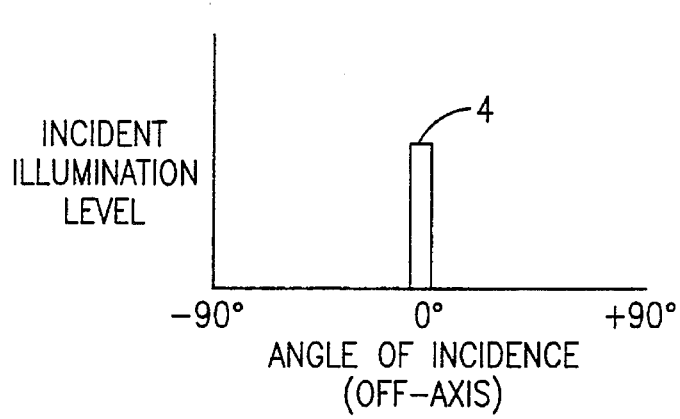
FIGS. 2, 4, and 6 depict Incident Angle Brightness Histograms, which are graphs plotting incident illumination level as a function of angle of incidence, associated with the lighting geometries depicted in FIGS. 1, 3, and 5 respectively.
Figure 9:
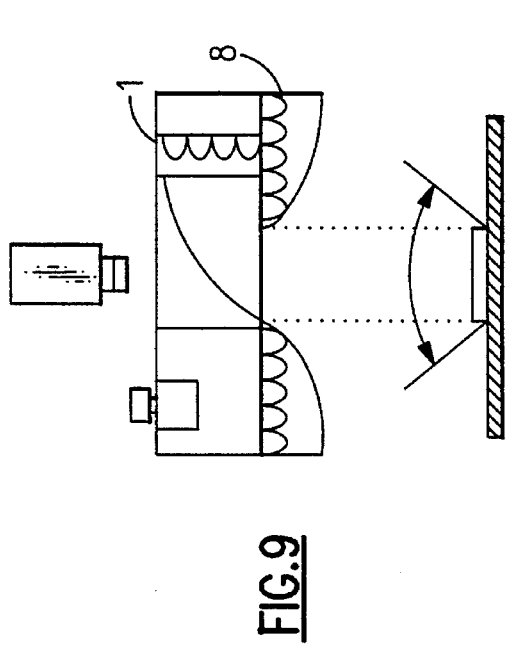

FIG. 9 depicts another embodiment of the invention wherein the co-axial illumination system 1 of FIG. 1 is combined with the ring illumination system 8 of FIG. 5 in order to create a continuous diffuse ring illumination system. The lighting environment created by this system is shown by the incident angle brightness histogram shown in FIG. 10, wherein a substantially uniform incident illumination level is produced over a specific region whose shape and size is dependent upon the shape and size of the ring illumination system.

Figure 9A:
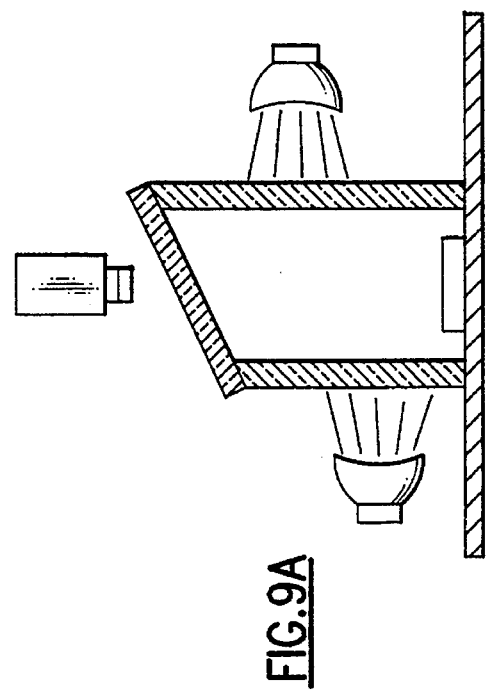
Figure 10:
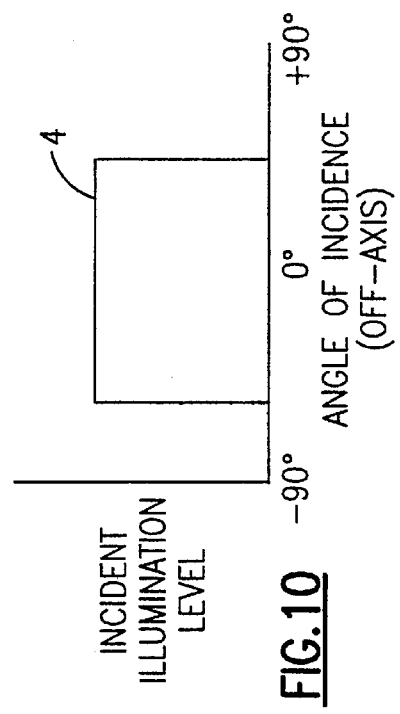
Figure 10A:
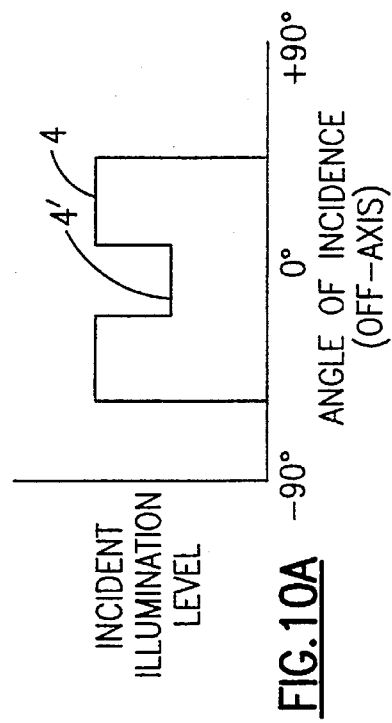

FIG. 9A shows a simple, cylindrical diffuse illumination system that approximates the results obtained using the embodiment of FIG. 9. This embodiment comprises an off-illumination-axis diffuse lighting cylinder. In this embodiment, the secondary diffuse light source is replaced with a simple beam splitter that is angularly located in the observation window that is formed by a top opening in the cylinder. This beam splitter arrangement thus operates to reflect a portion of the diffuse light projected through the off-observation-axis diffuse lighting cylinder, while at the same time allowing vision access to the object being observed by an observation means that is located outside of the diffuse lighting cylinder. This embodiment results in a lighting environment with the incident angle brightness histogram shown in FIG. 10A. This environment is characterized by a diffuse illumination zone 4 similar to that of FIG. 10. However, this lighting environment exhibits a diffuse illumination zone 4 with a brightness level reduced in proportion to the transmissivity of the beam splitter employed much like the lighting environment created by the embodiment of FIG. 7A, the zone of reduced brightness 4' corresponding to the angles of incidence associated with the beam splitter.

Figure 11:
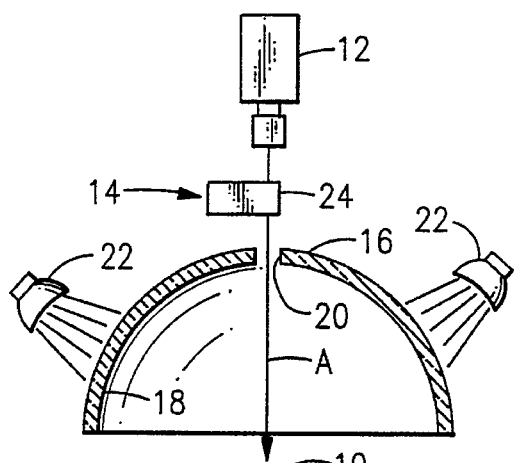
FIG. 11 is a schematic elevational view of the basic apparatus and relationships thereof permitting the practice of the invention with a back lighted translucent dome diffused light primary source.

A simplified schematic arrangement of components illustrating one embodiment of the inventive concepts is shown in FIG. 11, wherein the object to be viewed by a machine vision television camera is indicated at 10. The object 10, which normally, in the practice of the invention, would include a shiny or specular surface, such as the soldered surfaces of a printed circuit board, or a spherical ball beating, reflective packaging surface, or the like, and often is of an irregular or non-flat configuration, is viewed by a camera indicated at 12. The viewing of the object 10 by the camera 12 occurs along the observation axis A as indicated in FIG. 11. Usually, the purpose of viewing the object 10 by the camera 12 is for the purpose of inspecting the object 10 for flaws; however, the observation may be for any desired reason, such as for purposes of machining orientation or assembly prior to subsequent machining operations, or reading printed, inscribed or chemical or laser etched artwork. The concepts of the invention are particularly suitable for flaw detection in that a truly uniform lighting of the object 10 is achieved wherein significant variations in light reflected from the object will result only from localized surface slopes greater than half the incident illumination angle, such as are commonly associated with surface imperfections, and not undesired reflections from normal deviations in surface geometry that are not associated with defect conditions.

In accord with the concepts of the invention, a light projector 14 is incorporated between the object 10 and the camera 12 within the observation axis A, and a substantially uniform primary illumination of the object 10 is achieved by a translucent back light hemispherical dome or envelope 16 located over the object 10 as will be appreciated from FIG. 11. The translucent dome 16 may be formed of clouded or treated glass, or may be synthetic plastic or the like whereby light passing therethrough is uniformly diffused. The dome includes an inner surface 18 disposed toward the object 10 and an observation window or opening 20 is formed in the dome 16 to accommodate the observation axis A. The dome 16 is illuminated from the rear by a plurality of lamps 22 casting light upon the outer surface of the dome 16 and this light is diffused and emits from the inner surface 18 upon the object 10 to uniformly illuminate the object 10 for observation by the camera 12.

If the object 10 includes a shiny, specular surface, as occurs when viewing solder, ball bearings, reflective packaging, and the like, the surface of such an object will reflect the image of the dome observation window or opening 20 through which the camera viewing occurs along axis A. As no light is emitting from the window 20 with a conventional illuminating dome, the window 20 will appear as a dark or dead spot in the dome 16 which will be observed by the camera 12, and the camera will sense the dark reflection of the window 20 as a defect, unless the camera output is programmed to ignore this window reflection. If the camera program ignores the window reflection, an imperfection on the object 10 coinciding with the observation axis A will not be sensed by the camera 12 permitting a flawed object to pass inspection.

To overcome the aforedescribed problems resulting from the reflection of the window 20, the light projector 14 projects diffused light through the window 20 upon the object 10 along the observation axis A. In this manner, the window 20 no longer appears as a dark spot upon the inner surface 18 of the dome 16, and as the projected light emitting from the beam splitter 14 is of an intensity and character substantially equal to the primary diffused light passing through the dome 16 as generated by the lamps 22, the dome 16 is free of dark or dead spots and a true uniform illumination of the object 10 is achieved and defects on the object 10 coinciding with the observation axis A will be detected by the camera 12.

Figure 12:
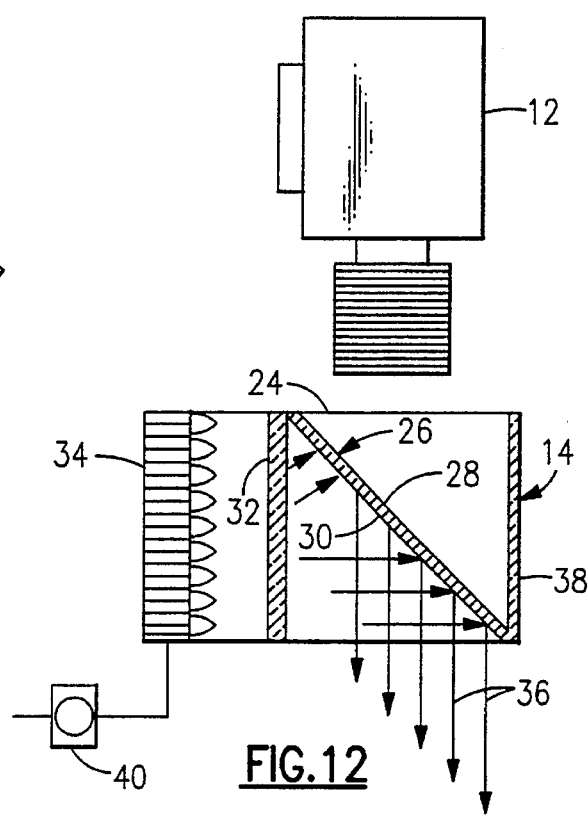
FIG. 12 is an enlarged detail view of the beam splitter and television camera used in the practice of the invention, the beam splitter being shown in this section.
Figure 12A:
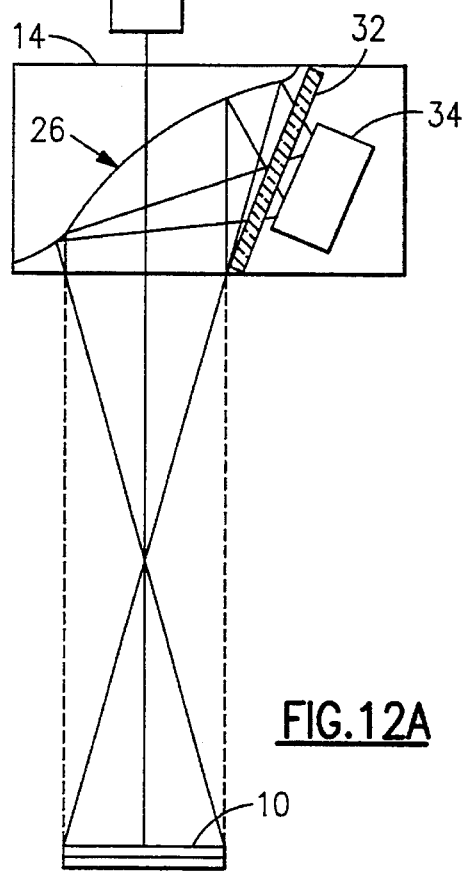
FIG. 12A is an enlarged detail of a curved beam splitter used in the practice of the invention, the beam splitter being shown in this section.

In the preferred embodiments, the light projector 14 is a beam splitter and includes a housing 24 in which a mirror 26 is located. The mirror 26 may be disposed at an angle with respect to the observation axis A, and the mirror includes a face 28 disposed toward the camera 12 and a face 30 disposed toward the object 10. The surfaces 28 and/or 30 are conventionally provided with silvered strips, or otherwise treated, wherein the mirror 26 constitutes both a reflective surface and a light pervious surface wherein light may pass through the mirror 26 from the object 10 for observation by the camera 12, and the mirror 26 also reflects the diffused light generated by the beam splitter light source, as later described. Alternatively, the beam splitter mirror 26 can be formed by a half silvered membrane pellicle of nitrocellulose or plastic material, such as "MYLAR", which has advantageous beam splitting characteristics in certain applications. Either material used as the beam splitter mirror 26 may be provided in a curved configuration having a concave face disposed towards both the object 10 and the light source 34 and a convex face disposed towards the the observation means, which may be a machine vision camera, as shown in FIG. 12A. This configuration provides an increased range of incident angles for the on-observation axis diffused light source while at the same time a reducing height of the light projector 14.

The light projector 14 includes at least one translucent light diffusion panel 32 formed of treated glass, plastic, or other light translucent material capable of evenly diffusing light cast upon the panel 32 by the light source 34. The light source 34 may consist of a plurality of lamps, diodes, or optical fibers, capable of generating a relatively uniform panel of light cast upon the diffuser 32, and such diffused light illuminates the mirror 26 and is projected in the direction 36 indicated by the arrows, which constitutes the observation axis A. It will be appreciated that the light direction 36 is coaxial with and coincides with the observation axis A. The size of the mirror 26 is such that the diffused light reflected therefrom along arrows 36 is sufficient to completely occupy the observation window 20 such that the window 20 will be "filled" with the diffused light emitting from diffuser panel 32 and light source 34. It will be understood that the light projector 14, light source 34 and translucent light diffusion panel 32 may be adjusted in size, shape and relative proximity to create continuous uniform illumination across objects of different sizes or at different working distances.

The light projector 14 includes a light absorbing panel 38, and the intensity of the light generated by the light source 34 is adjustable by the light control rheostat 40 to ensure that the intensity and the character of the light 36 will be substantially equal to the primary light diffused by the dome 16 and cast upon the object 10 by the lamps 22.

The light projector 14 is similar in many respects to that shown in my U.S. Pat. No. 5,187,611, and the beam splitter concepts shown in this patent are applicable in the instant application.

By regulating the light control 40, the light 36 projected through the window 20 will equal in intensity and character the other light being cast upon the object 10, and the use of the inventive concepts completely eliminates false readings which would otherwise be picked up by the camera 12 due to the reflection of the window 20, and the camera therebehind, as reflected by the surface of the object 10. In the practice of the invention, the window 20 is neutralized and a truly continuous diffused light source of the object 10 is achieved eliminating false readings by the camera 12 and permitting a true 100% inspection of that side of the object 10 observable by the camera 12.

Figure 13:
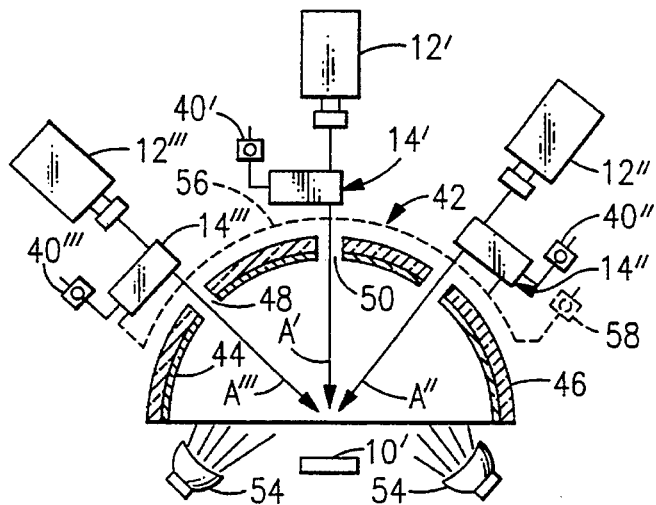
FIG. 13 is a schematic illustration of apparatus practicing the principles of the invention wherein the diffused light illumination dome employs an inner light diffusing surface and an outer light reflecting surface, and a plurality of cameras and observation orifices are employed.

A variation of the inventive concepts is shown in FIG. 13. In FIG. 13, three dome observation windows, cameras and light projectors permit viewing of the object from various angles, and the diffused light source dome is interiorly lighted to produce a more concise assembly of components than that possible with the arrangement shown in FIG. 11.

In the embodiment of FIG. 13, components similar to those previously described are indicated by primes, and these components function in a manner identical to that described above.

In FIG. 13, the illuminating dome 42 is located above the object 10' to be observed, and the dome 42 includes an inner hemispherical layer 44 of diffuse reflective paint. The construction is such that light cast upon the layer 44 interior of the dome 42 is diffusely reflected inwardly upon the object 10', providing a primary illumination effect similar to that achieved with the embodiment of FIG. 11.

The dome 42 is provided with three observation windows as indicated at 48, 50 and 52, and opening 50 is associated with a camera 12' and light projector 14', while opening 52 provides an observation window for camera 12" and light projector 14", while window 48 provides access for the observation axis A''' of the television camera 12''' as associated with the light projector 14'''.

The primary light source for the dome 42 is provided by the lamps 54 located adjacent the object 10' and directed toward the interior of the dome 42 such that the reflective layer 44 receives the light emitting from the lamps 54 and the light reflected from the layer 44 is diffused by layer 44 for illuminating the object 10' with a uniform diffused light. By locating the lamps 54 adjacent the object 10' the overall dimensions and relationship of components is more concise than the illustrated embodiment of FIG. 11, and size and configuration advantages exist with the embodiment of FIG. 13.

The light projectors 14', 14", and 14''' of the embodiment of FIG. 13 may utilize separate lamp controlling rheostats 40', 40" and 40''', respectively, whereby the various light projectors are separately controllable so that any minute light variations that may occur at the window 48, 50 and 52 may be accommodated. However, it is also possible to connect the light sources of the three light projectors in parallel by a circuit 56, as represented in dotted lines in FIG. 13, controlled by a single rheostat 58.

The concepts of the operation of the embodiment of FIG. 13 are identical to those described above with respect to FIG. 11. The observation axis of each of the three cameras is directed toward the object or objects of interest 10', and the dome observation window through which each camera observation axis extends is filled with diffused light projected from the associated light projector so as to eliminate any false readings which would otherwise exist due to the reflection from the surface of the object 10' of the windows 48–52. With conventional illumination domes, the existence of a plurality of cameras to permit viewing of the object from various angles also resulted in a plurality of reflected dark spots due to the presence of the observation windows in the dome increasing the likelihood of false readings, and the possibility of overlooking flaws in the observed object. In the practice of the invention regardless of the number of windows formed in the dome a continuous light source for the observed object is provided and any shadows or dark reflections from the object 10' will represent flaws, and not reflections from non-uniformities in the illuminating dome structure itself.

In FIGS. 14–16, another embodiment for illuminating an object with diffused light utilizing the concepts of the invention is illustrated. In this embodiment, an envelope or dome generally indicated at 60 is formed of either an opaque material or a translucent material having a lower bell configuration having an outer surface or layer 61 and an inner surface or layer 63. The layer 61 is internally silvered, or the like, to function as a mirror or efficient reflector of light, and the inner surface 63 constitutes a light diffusing layer whereby light within the dome 60 will be reflected by the layer 61 and diffused by the layer 63. The dome 60 includes a lower annular edge 62, and its upper regions include a cylindrical neck 64 open at opening 66. An annular aperture 68 is defined within the dome 60 at the upper region of the bell portion, and an electronic camera, such as a television camera, not shown, is adapted to be located above the dome 60 having an observation axis coaxial with the axis of the dome 60 as represented by dotted lines 70. The observation axis as represented by lines 70 is in alignment with the light reflecting object to be illuminated and viewed as shown at 72.

A beam splitting partially silvered mirror 74 is mounted within the neck 64 disposed at an angle to the observation axis. The mirror 74 may be embedded into the neck 64 as at 76, or otherwise attached to the neck. A plurality of lamps 78, which may constitute diodes, incandescent lamps, or the like, are mounted exteriorly of the neck 64 upon a bracket 88, attached to the neck 64 by pins 84, FIG. 5.

The dome neck 64 is translucent and constitutes a light diffuser whereby the light entering the neck 64 emitting from lamps 78 is diffused prior to being reflected from the mirror 74. Light passing through the partially silvered beam splitter 74 passes through the opening 80 formed in neck 64 which is in opposed relationship to the lamps 78, and a light absorbing panel 86 is mounted upon the bracket 82 for absorbing light emitting from lamps 78 passing through the mirror 74. Bracket 82 is attached to neck 64 by the pins 84. Of course, it will be appreciated that the light reflecting surface 61 defined on the bell portion of the dome 60 does not extend to the exterior surface of the neck 64 as it is necessary that light emitting from lamps 78 enter the neck 64 and a portion of such light is reflected from the mirror 74 downwardly along lines 70 upon the viewed object 72.

An annual ring 90 is attached to the lower end of the dome 60 adjacent the lower edge 62 by a plurality of fasteners 92. The cross sectional configuration of the ting 90 will be appreciated from FIG. 4, and the ring includes an inwardly radially projecting lip upon which an annular reflecting surface 94 is formed. The reflecting surface 94 may be silvered to increase its light reflecting capabilities, and the surface 94 is obliquely related to the horizontal whereby light impinging on the surface 94 will be reflected internally into the bell portion of the dome 60. The ting may also be made of translucent material machined to a thickness causing the light diffusely transmitted through the ring to be equal in intensity to the light reflected off of the inside of the bell portion of the dome.

A plurality of lamps 96 are mounted within the ring 90 evenly spaced about the circumference of the ring as will be appreciated from FIG. 6. The lamps 96 directly illuminate the reflecting surface 94 and the lamp light is efficiently reflected into the dome 60 for passing through the diffusing layer 63, reflected from the reflecting layer 61 and upon the object 72 wherein the object 72 is prevented from being directly illuminated by the lamps 96. Accordingly, all of the light illuminating object 72 will be diffused light as reflected by surface 61 and diffused by layer 63.

Rheostats, or other lamp control means, not shown, may be used to control the intensity and character of the light emitting from lamps 78, as described with respect to the above embodiments.

The apparatus of FIGS. 14–16 functions in a manner similar to that described above with respect to the embodiments of FIGS. 11 and 13. The lamps 78 are illuminated whereby diffused light will be reflected from beam splitter mirror 74 upon object 72. The electronic television camera, not shown, produces an observation axis as represented by dotted lines 70 for viewing the object 72. Primary illumination of the object 72 results from the lamps 96 whose light is reflected into the bell portion of the dome 60 and the resultant diffused light illuminates object 72. By controlling the intensity of the lamps 78, the light entering the bell portion of the dome 60 through the aperture 68 as reflected by the mirror 74 can be adjusted such that the reflected diffused light is substantially equal in intensity and character to that reflected by layer 61 as diffused by layer 63, and hence, the illumination apparatus of FIGS. 14–16, also, illuminates any "dark spot" at the aperture 68 preventing a dark reflection from the light reflecting object 72 which would be sensed by the camera and produce an erroneous and misleading signal as to the character of the surface of the object 72. The embodiment of FIGS. 14–16 is concise, rugged, and readily lends itself to many applications.

Of course, the reflector dome 60 could be constructed in a manner different than that disclosed above. For instance, the bell portion of the dome could be formed of turned or spun aluminum having an internal light diffusing reflecting surface and the tubular neck can be formed of a translucent material and mechanically attached to an aluminum bell portion. Further, the beam splitter mirror 74 can be formed by a half silvered membrane pellicle of nitrocellulose or plastic film, such as "MYLAR", which has advantageous beam splitting characteristics in certain applications.

Figure 17:
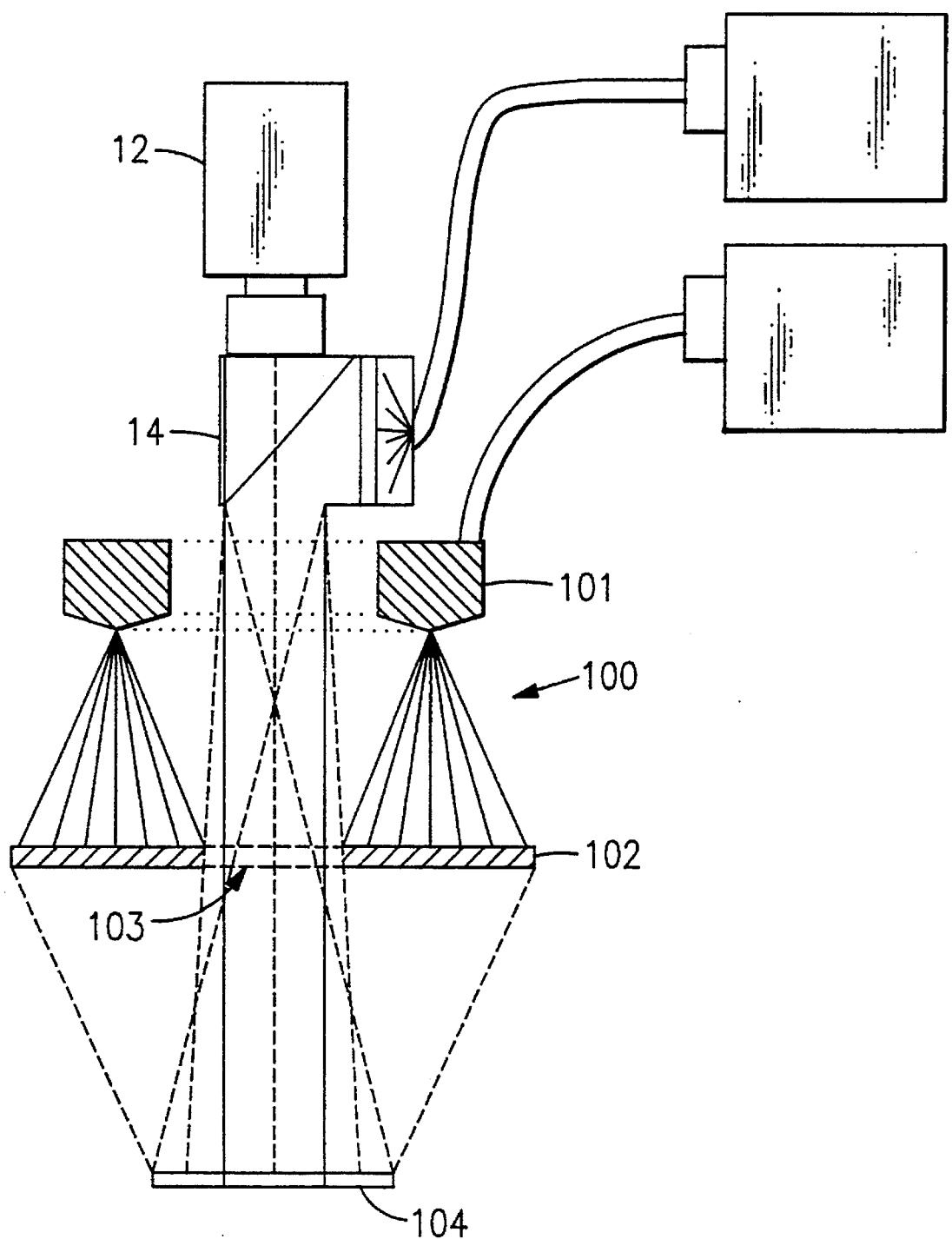
FIG. 17 is a schematic elevational view of another embodiment of the apparatus and relationships thereof permitting the practice of the invention with a back lighted translucent ring-shaped diffused primary light source.

A further embodiment of the inventive concept is shown in FIG. 17. In FIG. 17, the camera 12 and light projector 14 operate in like manner as those described earlier for the other embodiments of the inventive concept previously disclosed. However, the primary off-observation axis diffuse light envelope or dome is replaced by a primary off-observation axis ring illuminator 100. The ring illuminator 100 is comprised of light source 101 and a diffuser ring 102. The light source may be a fiberoptic ring illuminator, an LED array illuminator, or even a standard flourescent ring lamp. Similar to the primary diffuse light envelopes or domes described above, the diffuser ring 102 also has an observation window 103 disposed therein to provide vision access, along an observation axis to the area 104 being observed by the camera 12. The light projector 14 effectively "fills the hole" in the primary diffuse light source created by the observation window 103 with diffused light that can be adjusted such that it is substantially equal in intensity and character to that provided by the ring illuminator.

Figure 18:
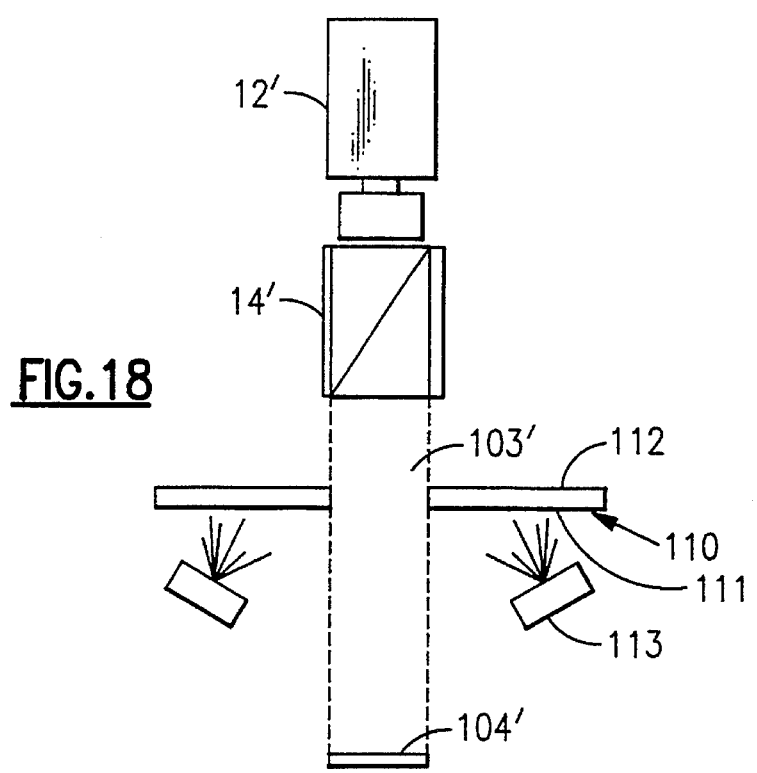
FIG. 18 is a schematic illustration of an apparatus practicing the principles of the invention wherein the diffused ring illuminator employs an outer light reflecting surface.

Another variation of the inventive concepts is shown in FIG. 18. In FIG. 18, a diffuse reflector 110 takes the place of the diffuser ring utilized in the embodiment shown in FIG. 17 and the diffuse reflector is interiorly lighted by light source 113 to produce a more concise assembly of components that is possible with the arrangement shown in FIG. 17. In the embodiment of FIG. 18, components similar to those previously described are indicated by primes, and these components function in a manner identical to that described above.

In FIG. 18, the diffuse reflector 110 is located above the area 104' that is to be observed and the diffuse reflector 110 includes an inner layer 111 that is translucent and capable of diffusing light reflected by the diffuse reflector outer layer 112, which may be in the form of a mirror. The construction of the layers 111 and 112 is such that light cast upon the inner layer 110 of the diffuse reflector 110 is reflected from the outer layer 112 throught the translucent layer 111 which diffuses the light relected from outer layer 112 such that the light relected inwardly upon the area to be observed 104' is uniformly diffused proding a primary illumination effect similar to that achieved with the embodiment of FIG. 17.

The concepts of the operation of the embodiment of FIG. 18 are identical to those described with respect to those previously described. The observation axis of the camera is directed toward an area to be observed 104', and the ring illuminator observation window through which the camera observation axis extends is filled with diffused light projected from a light projector so as to eliminate any false readings which would otherwise exist due to the reflection from the surface of the area of the observation window 103'.

Figure 19:
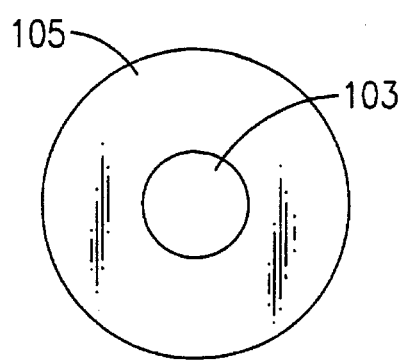
FIG. 19 is an end view of an off-axis ring illuminator geometry particularly suited for viewing circular shaped objects or areas.
Figure 20:
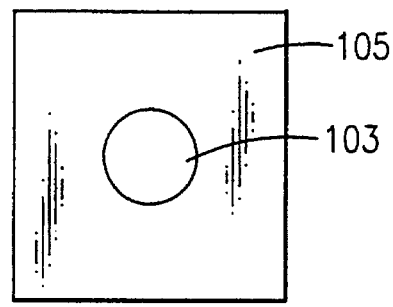
FIG. 20 is an end view of an off-axis ring illuminator geometry particularly suited for imaging square objects or areas.
Figure 21:
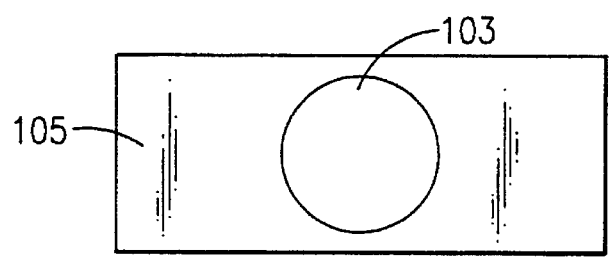
FIG. 21 is an end view of an off-axis ring illuminator geometry particularly suited for imaging rectangular shaped objects or areas.

The ring illuminator used in either of the embodiments depicted in FIGS. 17 or 18 has a perimeter shape and size that correlates to the viewing geometry, the aperture size of the viewing optics, and the size of the area being observed. A variety of ring illuminator geometries are shown in FIGS. 19–21. For example, the geometry shown in FIG. 19 is particularly suitable for viewing circular shaped areas. The geometry shown in FIG. 20 is suited for viewing square shaped areas and the geometry shown in FIG. 21 is preferable for viewing rectangular shaped areas. Each of these illuminators has an on observation axis observation window 103 through which an on-observation axis light source is projected and a primary off-observation axis illumination area 105.

Figure 22:
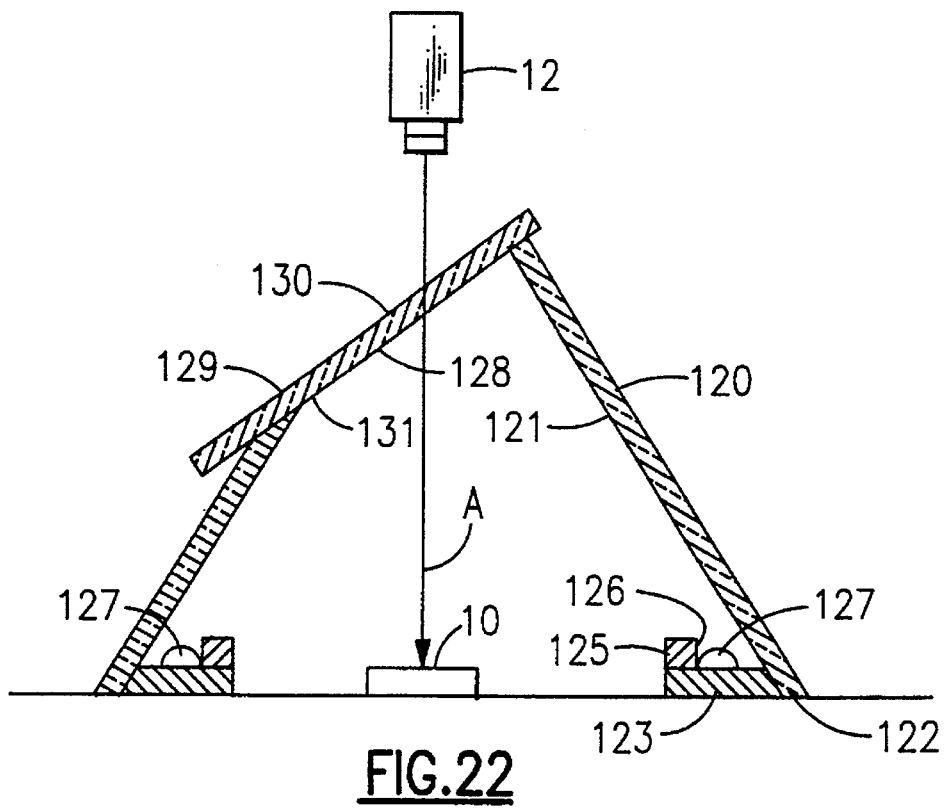
FIG. 22 is a schematic elevational view of a simple embodiment of an apparatus and the relationships thereof permitting the practice of the invention with a back lighted translucent cone diffused primary light source and an angled beam splitter located in line with the observation axis.
Figure 23:
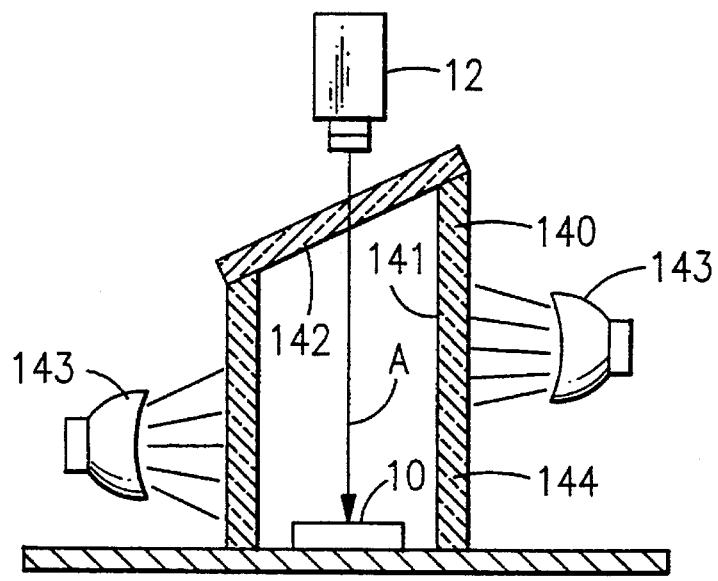
FIG. 23 is a schematic elevational view of yet another simple embodiment of the apparatus and relationships thereof permitting the practice of the invention utilizing a back lighted translucent tube-shaped diffused primary light source and angled beam splitter located in line with the observation axis.

Two further embodiments of the inventive concept are shown in FIGS. 22 and 23. Both of these embodiments utilize simple lighting geometries and single off-observation axis diffuse light sources to approximate the lighting environments obtained using the embodiments of the invention that require the use of multiple diffuse light sources.

In FIG. 22, the viewing of the object 10 by the camera 12 occurs along the observation axis A. A substantially uniform illumination of the object 10 is achieved by a cone or dome lighting envelope 120 located over the object 10 as will be appreciated from FIG. 22. The cone 120 includes an inner layer of diffuse reflective paint 121. The construction is such that the light cast upon the layer 121 interior of the cone 120 is diffusely reflected inwardly upon the object 10.

Similar to the embodiment shown in FIGS. 14–16, the cone 120 includes a lower annular edge 122. An annular ring 123 is attached to the lower end of the cone 120 adjacent the lower edge 122 by an attachment means, which may be a plurality of fasteners or any other suitable means such as glue or the like. The cross sectional configuration of the ring 123 will be appreciated from FIG. 22, and the ring includes an inwardly projecting lip 125 upon which an annular reflecting surface 126 is formed. The inner layer 121 is obliquely related to the horizontal whereby light impinging on the inner layer 121 will be diffusely reflected internally into the cone 120. Alternatively, the lip 125 may be constructed from a translucent material machined to a thickness such that light diffusely transmitted therethrough is equal in intensity to the light reflected off the inner layer of the cone.

The light source for the cone 120 is provided by a plurality of lamps 127 mounted within the ring 123. The lamps 127 are evenly spaced about the circumference of the ring. The lamps directly illuminate the inner layer 121 of the cone 120 and the lamp light is efficiently reflected by the inner layer and upon the object 10 so as to substantially uniformly illuminate the object for observation by the camera 12.

The cone includes an angular observation window or opening 128 formed in the cone 120 by cutting off the top portion of the cone by a plane at an angle with respect to the observation axis A selected to reflect a portion of the light reflected by the inner layer 121 of the cone 120. The angle may be preferably substantially 45 degrees.

A beam splitter mirror 129, similar to the mirror described previously herein, is mounted at the angular observation window. The mirror 129 includes a face 130 disposed toward the camera 12 and a face 131 disposed toward the object 10. The surfaces 130 and/or 131 are conventionally provided with silvered strips, or otherwise treated, wherein the mirror 129 constitutes both a reflective surface and a light pervious surface wherein light may pass through the mirror 129 from the object 10 for observation by the camera 12, and the mirror 129 also reflects the diffused light reflected off of the inner layer 121 of the cone 120. Thus a substantially uniform diffuse lighting environment is created using a single light source.

In FIG. 23, a back lighted translucent cylinder 140 takes the place of the cone or dome envelope utilized in the embodiment shown in FIG. 22. The translucent cylinder may be formed of clouded or treated glass, or may be synthetic plastic or the like whereby light passing therethrough is uniformly diffused. The cylinder includes an inner surface 141 disposed toward object 10 and an angular observation window or opening 142 formed in the cylinder by cutting off the top portion of the cylinder by a plane at an angle with respect to the observation axis A selected to reflect a portion of the light diffusely transmitted through the back lighted cylinder.

The cylinder 140 is illuminated from the outside by a plurality of lamps 143 casting light upon the outer surface 144 of the cylinder 140. This light is diffused by the cylinder material and emits from the inner surface 141 upon the object 10 to substantially uniformly illuminate the object 10 for observation by the camera 12.

It will be appreciated that the inventive concepts permit a truly continuous source of illumination for machine vision cameras to be achieved, and the invention permits an accurate viewing and evaluation of the observed object free of error producing shadows or reflections.

It is appreciated that various modifications to the inventive concepts may be apparent to those skilled in the art without departing from the spirit and scope of the invention.

We claim:

1. A diffuse lighting device for uniformly illuminating a desired portion of an object (10, 72) when observed along an observing axis extending through an object observing location, said diffuse lighting device comprising:

a surface, for supplying light, defining an opening (20, 48, 50, 52, 68, 103) through which the observing axis (A, 70) passes, said surface being arranged to supply primary diffused light (22, 54, 96, 101, 113, 127, 143) to provide said uniform illumination of the desired portion of the object (10, 72), when placed at the observing location and viewed along said observing axis, except for a portion of the object (10, 72) effected by the opening;

a source (34, 78) for producing secondary diffused light to illuminate the desired portion of the object effected by the opening; and a partially reflective mirror (14, 74, 129) for supplying said secondary diffused light (34 78) along the observing axis (A, 70) to uniformly illuminate each portion of the object (10, 72) effected by the opening to produce, when primary diffused light illuminates said surface, said uniform illumination of the desired portion of the object (10, 72) when viewed along the observing axis.

2. A diffuse lighting device according to claim 1 wherein said surface is a light diffuser and a primary light source (22, 54, 96, 101, 113, 127, 143) cooperates with said light diffuser to uniformly illuminate, with diffused light, the desired portion of the object (10, 72) except for a portion of the object (10, 72) effected by the opening when viewed along the observing axis, and said mirror (14, 74, 129) is positioned, along the observing axis (A, 70) at a location spaced from both the desired portion of the object and the opening, so as to supply said secondary diffused light along the observing axis (A, 70) to the desired portion of the object (10, 72) as well as supply light reflected by the desired portion of the object (10, 72) to an observation device, and said diffuse lighting device prevents said secondary diffused light from directly illuminating, during use, the desired portion of the object.

3. A diffuse lighting device according to claim 2 wherein a mechanism (40) is further provided for controlling illumination characteristics of at least one of said primary diffused light (22, 54, 96, 101, 113, 127, 143) and said secondary diffused light (34, 78) whereby light from said primary diffused light (22, 54, 96, 101, 113, 127, 143) reflected by the desired portion of the object (10, 72) to said mirror (14, 74, 129), will be substantially identical in intensity and character to said secondary diffused light (34, 78) reflected by the desired portion of the object (10, 72) to said mirror (14, 74, 129), so that uniform illumination of the desired portion of the object (10, 72), when viewed along the observing axis, is facilitated.

4. A diffuse lighting device according to claim 2 wherein said light diffuser comprises an envelope (16, 42, 60, 102, 120, 140) having a surface containing a reflective substance (44, 121) and said primary light source (22, 54, 96, 101, 113, 127, 143) is arranged to illuminate the reflective substance (44, 121) on the surface of the envelope whereby light from said primary light source (22, 54, 96, 101, 113, 127, 143) is reflected by the reflective substance to the desired portion of the object (10, 72).

5. A diffuse lighting device according to claim 4 wherein said envelope (16, 42, 60, 102, 120, 140) has an annular edge (62) remote from said opening (20, 48, 50, 52, 68, 103), said annular edge (62) supports an annular impervious shield, and said primary light source (22, 54, 96, 101, 113, 127, 143) is disposed peripherally about said annular edge (62) with said annular impervious shield located intermediate said primary light source (22, 54, 96, 101, 113, 127, 143) and the desired portion of the object (10, 72) to prevent the light generated by said primary light source (22, 54, 96, 101, 113, 127, 143) from directly illuminating the desired portion of the object (10, 72).

6. A diffuse lighting device according to claim 2 wherein said light diffuser comprises a translucent envelope (16, 42, 60, 102, 120, 140) at least partially surrounding the object (10, 72), said translucent envelope (16, 42, 60, 102, 120, 140) has outer and inner surfaces, and said primary light source (22, 54, 96, 101, 113, 127, 143) directly illuminates the outer surface of said translucent envelope (16, 42, 60, 102, 120, 140) whereby, during use, diffused light is emitted by the inner surface of said translucent envelope (16, 42, 60, 102, 120, 140) to the desired portion of the object (10, 72).

7. A diffuse lighting device according to claim 2, wherein said light diffuser defines a plurality of openings (48, 50, 52) with an observing axis (A', A", A'") extending through each said opening (48, 50, 52);

a plurality of sources of secondary diffused light; and a plurality of partially reflective mirrors (26, 74, 129), with one of said plurality of partially reflective mirrors (26, 74, 129) being associated with each one of said plurality of openings (48, 50, 52) for supplying light from one of said plurality of sources of secondary diffused light (34, 78) along one of the observing axis (A', A", A'").

8. A diffuse lighting device according to claim 2 wherein said primary light source (22, 54, 96, 101, 113, 127, 143) and said source of said secondary diffused light (34, 78) each include a light source selected from the group comprising a lamp, a plurality of diodes, an optical fiber, an array of LEDs and a fluorescent light.

9. A diffuse lighting device according to claim 1 wherein an attachment mechanism is further provided for attaching said diffuse lighting device to an observation device so that the observation device is positioned to receive light which is reflected from the desired portion of the object along the observing axis (A, 70) toward said mirror (14, 74, 129).

10. A diffuse lighting device according to claim 9 wherein the observation device is one of:

a machine vision camera (12);

a film camera; and a human observer.

11. A diffuse lighting device according to claim 1 wherein said mirror reflects said secondary diffused light (34, 78) along the observing axis (A, 70) toward the desired portion of the object (10, 72) and allows light reflected by the desired portion of the object (10, 72) to pass through said mirror (14, 74, 129) to be viewed by an observation device (12).

12. A diffuse lighting device according to claim 11 wherein a light absorbing member (38, 78) is remotely positioned from said source of said secondary diffused light (34, 78) for absorbing secondary diffused light (34, 78) which passes through said mirror (14, 74, 129).

13. A diffuse lighting device according to claim 1 wherein a secondary light diffuser (32) is positioned between said mirror (14, 74, 129) and said source of said secondary diffused light (34, 78) for providing diffused light to said mirror (14, 74, 129).

14. A diffuse lighting device according to claim 1, wherein said mirror (14, 74, 129) is one of:

a curved mirror (26); and a planar mirror (26, 74, 129).

15. A method of uniformly illuminating a desired portion of an object (10, 72) when observed along an observing axis extending through an object observing location, said method comprising the steps of:

defining an opening (20, 48, 50, 52, 68, 103) within a surface, for supplying light, through which the observing axis (A, 70) passes;

arranging said surface to supply primary diffused light (22, 54, 96, 101, 113, 127, 143) to provide said uniform illumination of the object (10, 72) when placed at the observing location and viewed along said observing axis, except for a portion of the object (10, 72) effected by the opening;

providing a source of secondary diffused light to illuminate the desired portion of the object; and supplying said second diffused light, via a partially reflective mirror (14, 74, 129), along the observing axis (A, 70) to uniformly illuminate the portion of the object (10, 72) effected by the opening to produce, when primary diffused light illuminates said surface, said uniform illumination of the desired portion of the object (10, 72) when viewed along the observing axis.

16. A method according to claim 15 further comprising the step of using a light diffuser as said surface and cooperating a primary light source (22, 54, 96, 101, 113, 127, 143) with said light diffuser to uniformly illuminate, with diffused light, the object (10, 72) except for a portion of the object (10, 72) effected by the opening when viewed along the observing axis, and positioning said mirror (14, 74, 129), along the observing axis at a location spaced from both the desired portion of the object and the opening, so as to supply said secondary diffused light along the observing axis to the desired portion of the object (10, 72) as well as supply light reflected by the desired portion of the object (10, 72) to an observation device, and preventing, via said diffuse lighting device, said secondary diffused light from directly illuminating, during use, the desired portion of the object.

17. A method according to claim 16 further comprising the step of utilizing an envelope (16, 42, 60, 102, 120, 140), having a surface containing a reflective substance (44, 121), as said light diffuser and arranging said primary light source (22, 54, 96, 101, 113, 127, 143) to illuminate the reflective substance (44, 121) so that light is reflected from said primary light source (22, 54, 96, 101, 113, 127, 143) to the desired portion of the object (10, 72) by the reflective substance.

18. A method according to claim 17 further comprising the step of providing said envelope (16, 42, 60, 102, 120, 140) with an annular edge (62) remote from said opening (20, 48, 50, 52, 68, 103), said annular edge (62) supporting an annular impervious shield, and disposing said primary diffused light (22, 54, 96, 101, 113, 127, 143) peripherally about said annular edge (62) with said annular impervious shield being located intermediate said primary diffused light (22, 54, 96, 101, 113, 127, 143) and the desired portion of the object (10, 72) to prevent the light generated by said primary diffused light (22, 54, 96, 101, 113, 127, 143) from directly illuminating the desired portion of the object (10, 72).

19. A method according to claim 16 further comprising the step of controlling illumination characteristics of at least one of said primary diffused light (22, 54, 96, 101, 113, 127, 143) and said secondary diffused light (34, 78), via an illumination control mechanism (40), whereby said primary diffused light (22, 54, 96, 101, 113, 127, 143) reflected by the desired portion of the object (10, 72) to said mirror (14, 74, 129), will be substantially identical in intensity and character to said secondary diffused light (34, 78) reflected by the desired portion of the object (10, 72) to said mirror (14, 74, 129), so that uniform illumination of the desired portion of the object (10, 72), when viewed along the observing axis, is facilitated.

20. A method according to claim 16, further comprising the step of utilizing a translucent envelope (16, 42, 60, 102, 120, 140), which at least partially surrounds the object (10, 72), as said light diffuser, said translucent envelope (16, 42, 60, 102, 120, 140) having outer and inner surfaces with said primary light source (22, 54, 96, 101, 113, 127, 143) directly illuminating the outer surface of said translucent envelope (16, 42, 60, 102, 120, 140) thereby emitting diffused light via the inner surface of said translucent envelope (16, 42, 60, 102, 120, 140) toward the desired portion of the object (10, 72).

21. A method according to claim 16, further comprising the step of defining a plurality of openings (48, 50, 52) in said light diffuser with one observing axis (A', A", A'") extending through each said opening (48, 50, 52) in said light diffuser;

providing a plurality of sources of secondary diffused light; and providing a plurality of partially reflective mirrors (26, 74, 129) with one of said plurality of partially reflective mirrors (26, 74, 129) being associated with each one of said plurality of openings (48, 50, 52) for supplying light from one of said plurality of sources of secondary diffused light (34, 78) along one of the observing axes (A', A", A'").

22. A method according to claim 16 further comprising the step of utilizing one of a lamp, a plurality of diodes, an optical fiber, an array of LEDs and a fluorescent light as said primary light source (22, 54, 96, 101, 113, 127, 143) and said source of said secondary diffused light (34, 78).

23. A method according to claim 15 further comprising the step of providing an attachment mechanism for attaching said light diffuser to an observation device so that the observation device is positioned to receive light which is reflected from the desired portion of the object along the observing axis (A, 70) toward said mirror (14, 74, 129).

24. A method according to claim 23 further comprising the step of utilizing one of:

a machine vision camera (12);

a film camera; and a human observer, as the observation device.

25. A method according to claim 15 further comprising the step of reflecting said secondary diffused light (34, 78), via said mirror (14, 26, 74, 129), along the observing axis (A, 70) toward the desired portion of the object (10, 72) and allowing light reflected by the desired portion of the object (10, 72) to pass through said mirror (14, 26, 74, 129) to be viewed by an observation device (12).

26. A method according to claim 25 further comprising the step of remotely positioning a light absorbing member (38, 78) from said source of said secondary diffused light (34, 78) for absorbing non-reflected light which passes through said mirror (14, 26, 74, 129).

27. A method according to claim 15 further comprising a step of positioning a secondary light diffuser (32) between said mirror (14, 74, 129) and said source of said secondary diffused light (23, 78) for providing diffused light to said mirror (14, 74, 129).

28. A method according to claim 15, further comprising the step of utilizing one of:

a curved mirror (26); and a planar mirror (26, 74, 129) as said mirror (14, 26, 74, 129).

29. A method of uniformly illuminating a desired portion of the object for observation along an observing axis extending through an object observing location, said method comprising the steps of:

defining an opening, through which the observing axis (A, 70) passes, in a surface;

placing the desired portion of the object at the observing location;

illuminating said surface to illuminate the desired portion of the object with primary diffused light to provide uniform illumination of the object, except for a portion of the desired portion of the object effected by the opening, when viewed along the observing axis;

illuminating a diffuser to indirectly illuminate the desired portion of the object with secondary diffused light supplied along the observing axis to illuminate uniformly the portion of the object effected by the opening, when viewed along the observing axis; and viewing the desired portion of the object along the observing axis with an observation device.

30. A method according to claim 29 further comprising the step of controlling illumination characteristics of said secondary diffused light and said primary diffused light so that the illumination characteristics of said secondary diffused light and said primary diffused light are equal to one another and the desired portion of the object is uniformly illuminated when viewed along the observing axis.

31. A method according to claim 30 further comprising the step of positioning a mirror along the observing axis at a location spaced from both the desired portion of object and the opening and supplying said secondary diffused light, via said mirror, along the observing axis and supplying light reflected by the desired portion of the object to be observed to the observation device via said mirror positioned along the observing axis.

32. A method according to claim 29 further comprising the step of reflecting light from said secondary diffused light, via said mirror, along the observing axis toward the desired portion of the object and allowing light reflected by the desired portion of the object to pass through said mirror to be viewed by an observation device.

* * * * *